United States Patent
Jung et al.

(10) Patent No.: US 8,435,548 B2
(45) Date of Patent: May 7, 2013

(54) PEPTIDE DERIVATIVES AND COSMETIC COMPOSITION COMPRISING THE SAME

(75) Inventors: Dai Hyun Jung, Gwangju (KR); Sang Hyun Moh, Suwon-Si (KR); Jung Hun Lee, Incheon (KR); Su Jung Kim, Gwangju (KR); Hyung Sik Kim, Incheon (KR); Hyo Hyun Seo, Incheon (KR); Yeon Ja Bae, Bucheon-si (KR)

(73) Assignee: Bio-FD&C Co., Ltd, Incheon (KR)

( * ) Notice: Subject to any disclaimer, the term of this patent is extended or adjusted under 35 U.S.C. 154(b) by 0 days.

(21) Appl. No.: 12/646,538

(22) Filed: Dec. 23, 2009

(65) Prior Publication Data
US 2010/0261879 A1 Oct. 14, 2010

(30) Foreign Application Priority Data
Apr. 13, 2009 (KR) .................. 10-2009-0031705

(51) Int. Cl.
*A61K 8/02* (2006.01)
(52) U.S. Cl.
USPC ........ 424/401; 514/18.6; 514/18.7; 514/18.8; 514/21.5; 514/21.6; 514/21.7; 514/21.8; 514/21.9; 514/741
(58) Field of Classification Search .................. None
See application file for complete search history.

(56) References Cited

U.S. PATENT DOCUMENTS
7,166,296 B2 * 1/2007 Houghten et al. ............ 424/450

FOREIGN PATENT DOCUMENTS
EP 1 481 669 A1 12/2004
EP 1 792 630 A1 6/2007
KR 10-2004-0049999 A 6/2004

OTHER PUBLICATIONS

Korkmaz, B et al; "Discriminating between the activites of human neutrophil elastase and proteinase 3 using serpin-derived fluorogenic substrates." J. Biol. Chem. (2002) 277(42) p. 39074-39081.*
Appeldoorn C. M. et al; "Rational optimization of a short human P-selectin binding peptide leads to nanomolar affinity antagonists." J. Biol. Chem. (2003) 278(12) 10201-10207.*
Kim, You-Jung; "Antimelanogenic and antioxidant properties of gallic acid." Biol. Pharm. Bull. (2007) 30(6) p. 1052-1055.*
Kong, Kwang-Hoon et al; "Expression and characterization of human tyrosinase from a bacterial expression system." Comp Biochem Physiol B (2000) 125 p. 563-569.*
European Patent Office, European Search Report issued in corresponding EP Application No. 09180600.0, dated Apr. 14, 2011.

* cited by examiner

*Primary Examiner* — Cecilia J Tsang
*Assistant Examiner* — Fred Reynolds
(74) *Attorney, Agent, or Firm* — Sughrue Mion, PLLC

(57) ABSTRACT

Disclosed are peptide derivatives, wherein glutathione-like peptides are connected to benzoic acid derivatives, and a cosmetic composition comprising the same. The peptide derivatives have excellent tyrosinase inhibition and anti-oxidative activities to show excellent skin whitening effect, biocompatibility without skin stimulation, and stability during long-term storage. Therefore, they can be effectively used for a cosmetic composition for skin whitening.

10 Claims, No Drawings

SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthetic glutathione-like peptide

<400> SEQUENCE: 1

Lys Glu Cys Gly
 1

<210> SEQ ID NO 2
<211> LENGTH: 3
<212> TYPE: PRT
<213> ORGANISM: Artificial Sequence
<220> FEATURE:
<223> OTHER INFORMATION: Synthetic glutathione-like peptide

<400> SEQUENCE: 2

Glu Cys Gly
 1

<210> SEQ ID NO 3
<211> LENGTH: 3
<212> TYPE: PRT
<213> ORGANISM: Artificial Sequence
<220> FEATURE:
<223> OTHER INFORMATION: Synthetic glutathione-like peptide

<400> SEQUENCE: 3

Tyr His Tyr
 1

<210> SEQ ID NO 4
<211> LENGTH: 4
<212> TYPE: PRT
<213> ORGANISM: Artificial Sequence
<220> FEATURE:
<223> OTHER INFORMATION: Synthetic glutathione-like peptide

<400> SEQUENCE: 4

```
Lys Tyr His Tyr
  1

<210> SEQ ID NO 5
<211> LENGTH: 10
<212> TYPE: PRT
<213> ORGANISM: Artificial Sequence
<220> FEATURE:
<223> OTHER INFORMATION: Synthetic glutathione-like peptide

<400> SEQUENCE: 5

Tyr Gly Gly Phe Leu Arg Lys Tyr Pro Lys
  1               5                  10
```

PEPTIDE DERIVATIVES AND COSMETIC COMPOSITION COMPRISING THE SAME

TECHNICAL FIELD

The present invention relates to peptide derivatives and a cosmetic composition comprising the same. More specifically, the present invention relates to peptide derivatives, which has an excellent skin whitening effect without any skin stimulation and good stability, and a cosmetic composition for skin whitening comprising the same.

BACKGROUND ART

Skin is a very important tissue, which protects a human body by being exposed to external environment and also has biochemical and physical functions. This tissue is composed of three primary layers: epidermis, dermis and hypodermis. The human skin color is determined depending on red blood cells in blood, carotene and melanin in combination, but the skin color differences between races or hyperpigmentation such as chloasma and freckle are mainly caused by melanin. The melanin residing in the epidermis, which is an outer skin layer, is synthesized by a process comprising the following steps: 1) an amino acid, tyrosine is converted into DOPA and then DOPA quinone by an enzyme tyrosinase, and 2) DOPA quinone is subjected to a non-enzymatic oxidation. It has a useful role in blocking ultraviolet light to protect the skin organ below the dermis.

However, the melanin, which is created by means of internal or external stress-based stimulus, is a stable substance which remains until it is discharged to the outside through a skin horning process even when the stress disappears. In addition, the melanin generation may increase through an in vivo polymerization-oxidation process using an enzyme such as tyrosinase as a catalyst when the generation of free radicals increases in skin, inflammatory response occurs, or UV light is applied. In particular, the UV light stimulates the melanin generation, and the partially increased melanin causes chloasma, etc., and undesired problem on skin aesthetically.

For this reason, as an inhibitor of melanin generation, hydroquinone, kojic acid, arbutin, glutathione or vitamin C (ascorbic acid), etc. has been used as a cosmetic ingredient, but theses inhibitors have disadvantages of unsatisfactory whitening effect, instability and severe skin stimulation.

TECHNICAL PROBLEM

In order to solve the above-mentioned problems of the prior arts, the present inventors have extensively studied, and as a result, they discovered that the peptide derivatives of the present invention, wherein glutathione-like peptides are connected to benzoic acid derivatives, have excellent tyrosinase inhibition effect suppressing the melanin generation with low skin stimulation and good stability during long-term storage.

Therefore, it is an object of the present invention to provide a peptide derivative having an excellent tyrosinase inhibition and anti-oxidative activities without any skin stimulation, and good stability during long-term storage.

It is another object of the present invention to provide a cosmetic composition for skin whitening comprising the peptide derivative.

TECHNICAL SOLUTION

One aspect of the present invention relates to a novel peptide derivative of formula (I), which may be used as an ingredient of functional cosmetics:

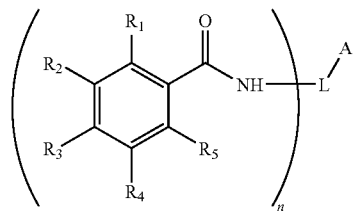

wherein, $R_1$ to $R_5$ are each independently hydrogen, hydroxy, $C_1$-$C_6$ alkyl, $C_1$-$C_6$ alkoxy, cyano, halo or amino, preferably, hydrogen or hydroxy;

n is 1 or 2, more preferably, 2;

L is absent or a linker, preferably, Lys; and

A is a glutathione-like peptide consisting of 3 to 12 amino acid residues.

Preferably, A is a glutathione-like peptide consisting of 3 to 12 amino acid residues comprising a peptide fragment of formula (II):

$$-X-Y-Z-\qquad(II)$$

wherein,

X is Glu, Gln, Asp or Asn, preferably, Glu;

Y is Cys; and

Z is Gly, Ala, Val, Leu, Ile or Phe, preferably, Gly.

Another aspect of the present invention relates to a peptide derivative of formula (III):

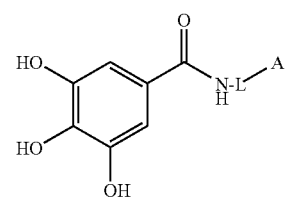

wherein,

L is absent or Lys, preferably, Lys; and

A is Glu-Cys-Gly.

Further aspect of the present invention relates to a peptide derivative of formula (IV):

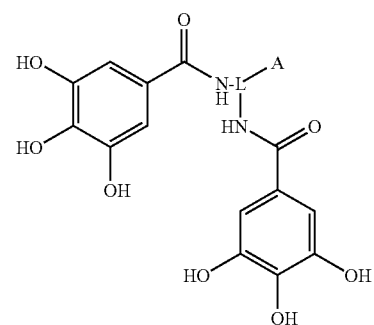

wherein,

L is absent or Lys, preferably, Lys; and

A is Glu-Cys-Gly.

The term "$C_1$-$C_6$ alkyl" as used herein means a straight or branched hydrocarbon having 1 to 6 carbon atoms, which includes methyl, ethyl, n-propyl, i-propyl and n-butyl, but is not limited thereto.

The term "$C_1$-$C_6$ alkoxy" as used herein means a straight or branched alkoxy having 1 to 6 carbon atoms, which includes methoxy, ethoxy and n-propanoxy, but is not limited thereto.

In this description, common rules for peptide nomenclature based on the single or three letter amino acid code apply unless mentioned otherwise. In other words, the central portion of the amino acid structure is represented by the three letter code (e.g., Ala, Lys) or one letter code (e.g., A, K), and L-configuration is assumed unless D-configuration is specifically indicated by "D-" followed by the three letter code (e.g., D-Ala, D-Lys).

The amino acid residues of the peptide can be nature or non-natural amino acid residues.

The peptide derivative of the present invention may be prepared by synthesizing the desired peptide, and coupling the peptide with a benzoic acid derivative.

The desired peptide may be prepared by extracting an in vivo protein and treating the protein with a protease to depolymerize, or using a genetic recombination and protein expression system, and preferably, prepared by a chemical synthetic method using a peptide synthesizer.

For example, the peptide derivative of the present invention may be prepared by a process comprising the steps of:

(1) obtaining a $NH_2$-protected peptide-resin by a common solid phase peptide synthesis (SPPS);

(2) reacting the obtained $NH_2$-protected peptide-resin with a benzoic acid derivative; and (3) removing the resin.

In the case that a functional group is located at a side chain of an amino acid residue of the desired peptide, in the step (1), the functional group-protected amino acid may be used to synthesize the peptide, and the protecting group attached to the functional group is removed in the step (3).

An exemplary process for preparing the peptide derivative according to the present invention using the functional group-protected amino acid is depicted in the following Reaction Scheme 1.

[Reaction Scheme 1]

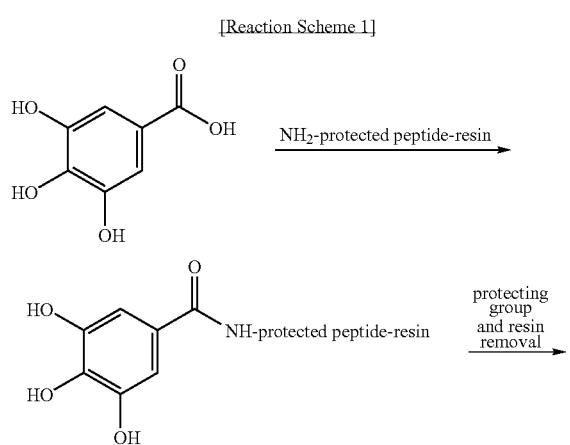

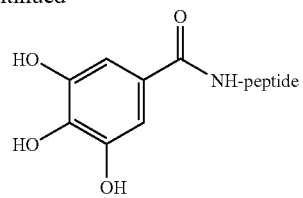

Further, another exemplary process for preparing the peptide derivative according to the present invention using the functional group-protected amino acid is depicted in the following Reaction Scheme 2.

[Reaction Scheme 2]

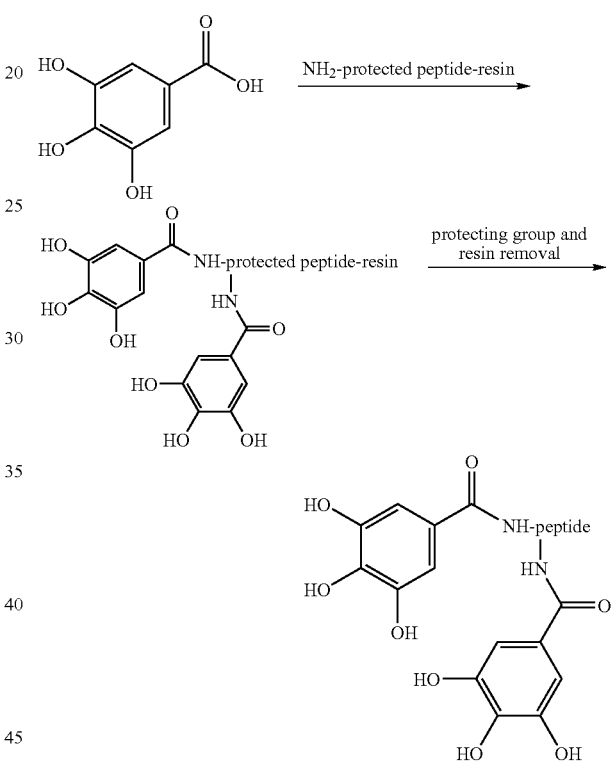

Further aspect of the present invention relates to a cosmetic composition, particularly a cosmetic composition for skin whitening, comprising the peptide derivative according to the present invention.

The peptide derivative of the present invention has a whitening effect by an inhibition activity of tyrosinase, which is related to the melanin generation. Further, the peptide derivative also has an anti-oxidative activity.

The cosmetic composition of the present invention may preferably contain the peptide derivative according to the present invention as an active ingredient in an amount of 0.001 to 10.0 wt %. The specific amount of the active ingredient may be properly decided depending on its purpose of use.

The cosmetic composition of the present invention may include common cosmetic ingredients typically used in the art, for example, common adjuvants such as antioxidant, stabilizer, solubilizer, vitamin, colorant and perfumery, and carriers besides the peptide derivative according to the present invention as an active ingredient.

The cosmetic composition of the present invention may be formulated to any form usually used in the art, for example, solution, suspension, emulsion, paste, gel, cream, powder, spray, etc.

In the case that the cosmetic composition is formulated as paste, cream or gel, the examples of the carriers include animal oil, vegetable oil, wax, paraffin, starch, tragacanth, cellulose derivative, polyethylene glycol, silicon, bentonite, silica, talc and zinc oxide, etc.

In the case that the cosmetic composition is formulated as powder or spray, the examples of the carriers include lactose, talc, silica, aluminum hydroxide, calcium silicate and polyamide power, etc., and especially in the case that the form is spray, additionally include propellant such as chlorofluorohydrocarbon, propane/butane and dimethylether.

In the case that the cosmetic composition is formulated as solution or emulsion, the examples of the carriers include solvent, solubilizer and emulsifier such as water, ethanol, isopropanol, ethyl carbonate, ethyl acetate, benzyl alcohol, benzyl benzoate, propylene glycol, 1,3-butylglycol oil, glycerol fatty acid ester, polyethylene glycol and sorbitan fatty acid ester, etc.

In the case that the cosmetic composition is formulated as suspension, the examples of the carriers include liquid diluent such as water, ethanol and propylene glycol, suspending agent such as ethoxylated isostearyl alcohol, polyoxyethylene sorbitol ester and polyoxyethylene sorbitan ester, microcrystalline cellulose, aluminum methahydroxide, bentonite, agar, tragacanth, etc.

The cosmetic composition of the present invention may be applied to cosmetics such as skin, lotion, cream, pack, coloring cosmetics, sun block cream, two-way cake, face powder, compact, makeup base, skin cover, eye shadow, lip stick, lip gloss, lip fix and eyebrow pencil.

ADVANTAGEOUS EFFECTS

The peptide derivatives according to the present invention, wherein glutathione-like peptides are connected to benzoic acid derivatives, have excellent tyrosinase inhibition and antioxidative activities to show excellent skin whitening effect, good biocompatibility without any skin stimulation, and stability during long-term storage.

In particular, the peptide derivatives of the present invention, wherein glutathione-like peptides are connected to benzoic acid derivatives through a linker, has better tyrosinase inhibition effect than the peptide derivatives, wherein glutathione-like peptides are directly connected to benzoic acid derivatives without any linker.

Therefore, the peptide derivative of the present invention can be effectively used for a cosmetic composition for skin whitening as a functional cosmetic ingredient.

BEST MODE

The present invention is further illustrated by the following examples, which are not to be construed to limit the scope of the invention.

Example 1

Preparation of Galloyl-Tetrapeptide(Lysyl-Glutamyl-Cysteinyl-Glycine) (SEQ ID NO: 1)

1.1: Synthesis of $NH_2$-Protected Peptide-Resin

The desired peptide was synthesized by the common solid phase peptide synthesis (SPPS) using 9-fluorenylmethoxycarbonyl (Fmoc) as an amino acid protecting group, and the amino acid residues thereof were extended by using N-hydroxybenzotriazole (HOBt) and N,N'-dicyclohexylcarbodiimide (DCC) as an activating agent [see: Wang C. Chan, Perter D. White, 'Fmoc solid phase peptide synthesis', Oxford].

Specifically, 0.04 g of glycine resin whose amino group is protected with Fmoc (Nova Biochem, Inc) was swollen in 3 ml of a solvent, N-methyl-2-pyrrolidone (NMP) for 20 min in a glass reactor, the solvent was removed, and Fmoc was removed by treating twice with 3 ml of 20% piperidine. The glycine resin whose Fmoc was removed was treated twice with dichloromethane (DCM) and twice with NMP, and reacted with a cysteine solution activated with HOBt-DCC at room temperature for about 2 hours. The above reaction procedure was sequentially repeated using glutamine and lysine to obtain a $NH_2$-protected peptide(lysyl-glutamyl-cysteinyl-glycine (SEQ ID NO: 1))-resin, which was washed twice with DCM, twice with NMP and twice with DCM, and then completely dried.

1.2: Synthesis of Galloyl-Tetrapeptide

The $NH_2$-protected peptide(lysyl-glutamyl-cysteinyl-glycine (SEQ ID NO: 1))-resin obtained above was reacted with 20% piperidine/NMP solution to remove the Fmoc attached to the amino group, washed with NMP and DCM, and subjected to a coupling reaction with 5 equivalents of gallic acid (Lancaster, Inc) at room temperature overnight. After the reaction was completed, the resin was washed several times with NMP and DCM, and dried.

The dried galloyl-tetrapeptide-resin was reacted with a mixture of trifluoroacetic acid:phenol:thioanisole:water:ethanedithiol (82.5:5:5:5:2.5 (v/v)) at room temperature for 2 to 3 hours to remove the functional group protecting groups, t-butyloxycarbonyl (Boc) and trityl (triphenylmethyl) and separate the galloyl-tetrapeptide from the resin. Then, the peptide was precipitated with cold diethylether.

The obtained galloyl-tetrapeptide was purified by reverse phase high performance liquid chromatography (column: Gemini, C18 110A 250×21.2 mm) using water containing 0.1% trifluoroacetic acid, and acetonitrile as a solvent.

Yield: 71%

Example 2

Preparation of Digalloyl-Tetrapeptide(Lysyl-Glutamyl-Cysteinyl-Glycine) (SEQ ID No: 1)

2.1: Synthesis of $NH_2$-Protected Peptide-Resin

The procedure of Example 1 was repeated to synthesize a $NH_2$-protected peptide(lysyl-glutamyl-cysteinyl-glycine (SEQ ID NO: 1))-resin.

2.2: Synthesis of Digalloyl-Tetrapeptide

The $NH_2$-protected peptide(lysyl-glutamyl-cysteinyl-glycine (SEQ ID NO: 1))-resin obtained above was reacted with 20% piperidine/NMP solution to remove the Fmoc attached to the amino group, washed with NMP and DCM, and subjected to a coupling reaction with 10 equivalents of gallic acid (Lancaster, Inc) at room temperature overnight. After the reaction was completed, the resin was washed several times with NMP and DCM, and dried.

The dried digalloyl-tetrapeptide-resin was reacted with a mixture of trifluoroacetic acid:phenol:thioanisole:water:ethanedithiol (82.5:5:5:5:2.5 (v/v)) at room temperature for 2 to 3 hours to remove the functional group protecting groups, t-butyloxycarbonyl (Boc) and trityl (triphenylmethyl) and separate the digalloyl-tetrapeptide from the resin. Then, the peptide was precipitated with cold diethylether.

The obtained digalloyl-tetrapeptide was purified by reverse phase high performance liquid chromatography (column: Gemini, C18 110A 250×21.2 mm) using water containing 0.1% trifluoroacetic acid, and acetonitrile as a solvent.
Yield: 62%
HPLC purity: >98%
Molecular weight: 739.7 ($M^++Na$: 760.5, $M^++K$: 776.4).

Example 3

Preparation of
Galloyl-Tripeptide(Glutamyl-Cysteinyl-Glycine)
(SEQ ID No: 2)

3.1: Synthesis of $NH_2$-Protected Peptide-Resin
The procedure of Example 1 was repeated to synthesize a $NH_2$-protected peptide(glutamyl-cysteinyl-glycine (SEQ ID NO: 2))-resin.
3.2: Synthesis of Galloyl-Tripeptide
The $NH_2$-protected peptide(glutamyl-cysteinyl-glycine (SEQ ID NO: 2))-resin obtained above was reacted with 20% piperidine/NMP solution to remove the Fmoc attached to the amino group, washed with NMP and DCM, and subjected to a coupling reaction with 5 equivalents of gallic acid (Lancaster, Inc) at room temperature overnight. After the reaction was completed, the resin was washed several times with NMP and DCM, and dried.
The dried galloyl-tripeptide-resin was reacted with a mixture of trifluoroacetic acid:phenol:thioanisole:water:ethanedithiol (82.5:5:5:5:2.5 (v/v)) at room temperature for 2 to 3 hours to remove the functional group protecting groups, t-butyloxycarbonyl (Boc) and trityl (triphenylmethyl) and separate the galloyl-tripeptide from the resin. Then, the peptide was precipitated with cold diethylether.
The obtained galloyl-tripeptide was purified by reverse phase high performance liquid chromatography (column: Gemini, C18 110A 250×21.2 mm) using water containing 0.1% trifluoroacetic acid, and acetonitrile as a solvent.
Yield: 69%

Comparative Example 1

Preparation of
Galloyl-Tripeptide(Tyrosyl-Histidyl-Tyrosine) (SEQ ID No: 3)

The procedure of Example 1 was repeated to obtain the title compound.
Yield: 76%

Comparative Example 2

Preparation of Digalloyl-Tetrapeptide(Lysyl-Tyrosyl-Histidyl-Tyrosine) (SEQ ID No: 4)

The procedure of Example 2 was repeated to obtain the title compound.
Yield: 71%

Comparative Example 3

Preparation of Galloyl-Decapeptide(Tyrosyl-Glycyl-Glycyl-Phenylalanyl-Leucyl-Arginyl-Lysyl-Tyrosyl-Prolyl-Lysine) (SEQ ID No: 5)

The procedure of Example 1 was repeated to obtain the title compound.
Yield: 59%

Test Example 1

Test of Inhibition Effect on Tyrosinase Activity

Inhibition effects of the prepared compounds were measured by the known method (see: Pomerantz S. H., *J. Biochem.*, 24:161-168, 1966).
The test compounds were prepared to a final concentration of 100 μM and put into a 96-well plate, and 220 μl of 100 mM sodium phosphate buffer (pH 6.8) and 40 μl of 1.5 mM L-tyrosine solution were added thereto. The resulting mixture was reacted with the addition of 20 μl of mushroom tyrosinase (1,500 units/ml, Sigma) at 37° C. for 20 min. 0.2 ml of the reacted solution was transferred to a 96-well plate, and its absorbance was measured at 490 nm with a microplate reader to obtain the inhibition effect on tyrosinase.
The tyrosinase inhibition effect was calculated according to the following formula 1 by using the absorbance of pure water as a control, and expressed as a percentage.

$$\text{Tyrosinase Inhibition (\%)} = 100 - \left(\frac{\text{Absorbance of each test compound}}{\text{Absorbance of control}}\right) \times 100 \quad \text{[Formula 1]}$$

The results are shown in Table 1.

TABLE 1

| Sample | Peptide derivative | Inhibition (%) |
| --- | --- | --- |
| Example 1 | Gallic acid-KECG | 40 |
| Example 2 | (Gallic acid)$_2$-KECG | 52 |
| Example 3 | Gallic acid-ECG | 34 |
| Comparative Example 1 | Gallic acid-YHY | 15 |
| Comparative Example 2 | (Gallic acid)$_2$-KYHY | 21 |
| Comparative Example 3 | Gallic acid-YGGFLRKYPK | 5 |
|  | Gallic acid | 10 |

As shown in Table 1, it was confirmed that the peptide derivatives of the present invention, wherein the glutathione-like peptide was connected to gallic acid, have significantly improved tyrosinase inhibition effects than gallic acid, and has better inhibition effects than the peptide derivatives of Comparative Examples 1 and 2, wherein a soy bean-derived peptide, which is known to have a good anti-oxidative activity, was connected to gallic acid or the peptide derivatives of Comparative Example 3, wherein a neuro peptide was connected to gallic acid. Further, the peptide derivative, wherein the glutathione-like peptide was connected to gallic acid through lysine, has better tyrosinase inhibition effect than the peptide derivative, wherein the glutathione-like peptide was directly connected to gallic acid.

Test Example 2

Free Radical Scavenging Activity Test
(Anti-Oxidative Activity Test)

Free radical scavenging activities of the galloyl-tetrapeptide and digalloyl-tetrapeptide prepared in Examples 1 and 2, respectively, were measured by a common DPPH method.
A representative antioxidant, vitamin C (Sigma) was used as a positive control, and the galloyl-tetrapeptide and digalloyl-tetrapeptide according to the present invention were mixed with 1,1-diphenyl-2-picrylhydrazyl (DPPH, Sigma)

producing free radicals in ethanol to determine the reduced amounts of the produced free radicals. Specifically, 0.4 ml of ethanol was mixed with 0.1 ml of the peptide derivative dissolved in purified water and 0.5 ml of 0.1 mM DPPH solution so that the final concentration of the peptide derivative was 10, 50 and 100 µM. The resulting solution was vigorously vortexed for 10 sec, kept at a dark cold place for 30 min, and then its absorbance was measured at 517 nm by ELISA method.

The anti-oxidative activity (free radical scavenging activity) was calculated according to the following formula 2 by using the absorbance of pure water as a control, and expressed as a percentage.

Free Radical Scavenging activity (%) = [Formula 2]

$$100 - \left( \frac{\text{Absorbance of each test compound}}{\text{Absorbance of control}} \right) \times 100$$

The results are shown in Table 2.

TABLE 2

| Concentration | Free radical scavenging activity (%) | | | |
|---|---|---|---|---|
| (uM) | Vitamin C | Gallic acid | Example 1 | Example 2 |
| 10 | 55.2 | 63.1 | 65.8 | 82.1 |
| 50 | 68.3 | 70.4 | 78.2 | 82.0 |
| 100 | 72.5 | 75.1 | 78.1 | 83.5 |

As shown in Table 2, the galloyl-tetrapeptide and digalloyl-tetrapeptide prepared in Example 1 and 2, respectively showed better free radical scavenging activities than vitamin C. Therefore, it was confirmed that the peptide derivatives of the present invention had excellent anti-oxidative activities.

While the invention has been described with respect to the above specific embodiments, it should be recognized that various modifications and changes may be made to the invention by those skilled in the art which also fall within the scope of the invention as defined by the appended claims.

The invention claimed is:

1. A peptide derivative of formula (I):

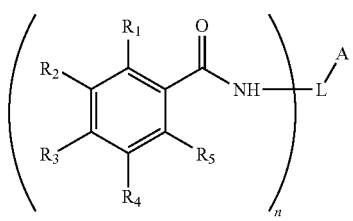

wherein, $R_1$ to $R_5$ are each independently hydrogen, hydroxy, a $C_1$-$C_6$ alkyl, $C_1$-$C_6$ alkoxy, cyano, halo or amino;

n is 1 or 2;

L is absent or a linker; and

A is a glutathione-like peptide consisting of 3 to 12 amino acid residues comprising a peptide fragment Glu-Cys-Gly.

2. The peptide derivative according to claim 1, wherein L is Lys.

3. The peptide derivative according to claim 1, wherein n is 2.

4. The peptide derivative according to claim 1, wherein $R_1$ to $R_5$ are each independently hydrogen or hydroxy.

5. The peptide derivative according to claim 1, wherein $R_1$ and $R_5$ are hydrogen, and $R_2$ to $R_4$ are hydroxy.

6. A peptide derivative of formula (III):

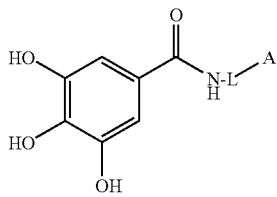

wherein,

L is absent or Lys; and

A is Glu-Cys-Gly.

7. The peptide derivative according to claim 6, wherein L is Lys.

8. A peptide derivative of formula (IV):

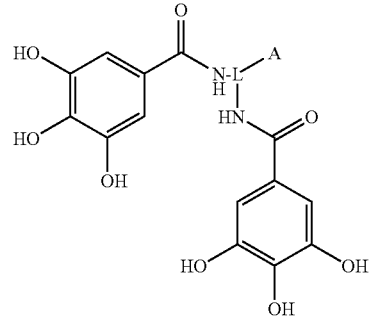

wherein,

L is Lys; and

A is Glu-Cys-Gly.

9. A cosmetic composition comprising the peptide derivative according to claim 1.

10. A cosmetic composition according to claim 9, which is used for skin whitening.

* * * * *